United States Patent
Crowley et al.

[11] Patent Number: 6,004,279
[45] Date of Patent: Dec. 21, 1999

[54] MEDICAL GUIDEWIRE

[75] Inventors: Robert J. Crowley, Wayland; Mark A. Hamm, Wakefield; Kevin R. Heath, Weston; Isaac Ostrovsky, Wellesley, all of Mass.

[73] Assignee: Boston Scientific Corporation, Natick, Mass.

[21] Appl. No.: 08/586,588

[22] Filed: Jan. 16, 1996

[51] Int. Cl.⁶ ..................................................... A61B 5/00
[52] U.S. Cl. ........................ 600/585; 600/433; 600/434
[58] Field of Search .................. 128/772, 657, 128/658; 604/95, 96, 280, 281, 282, 283

[56] References Cited

U.S. PATENT DOCUMENTS

| | | | |
|---|---|---|---|
| 3,841,308 | 10/1974 | Tate | 128/772 |
| 4,353,358 | 10/1982 | Emerson | 128/4 |
| 4,548,206 | 10/1985 | Osborne . | |
| 4,580,551 | 4/1986 | Siegmund et al. | 128/4 |
| 4,732,163 | 3/1988 | Bonello et al. . | |
| 4,798,598 | 1/1989 | Bonello et al. | 128/772 |
| 4,911,148 | 3/1990 | Sosnowski et al. | 128/6 |
| 4,940,062 | 7/1990 | Hampton et al. | 128/772 |
| 4,998,923 | 3/1991 | Samson et al. | 606/194 |
| 5,037,391 | 8/1991 | Hammerslag et al. | 604/95 |
| 5,095,911 | 3/1992 | Pomeranz | 128/662.06 |
| 5,095,915 | 3/1992 | Engelson | 128/772 |
| 5,114,402 | 5/1992 | McCoy | 604/95 |
| 5,165,421 | 11/1992 | Fleischhacker et al. | 128/772 |
| 5,228,441 | 7/1993 | Lundquist | 128/642 |
| 5,243,988 | 9/1993 | Sieben et al. | 128/662.06 |
| 5,315,996 | 5/1994 | Lundquist | 128/642 |
| 5,322,064 | 6/1994 | Lundquist | 128/642 |
| 5,329,923 | 7/1994 | Lundquist | 128/642 |
| 5,334,145 | 8/1994 | Lundquist et al. | 604/95 |
| 5,353,798 | 10/1994 | Sieben | 128/662.06 |
| 5,368,035 | 11/1994 | Hamm et al. | 128/662.06 |
| 5,373,619 | 12/1994 | Fleischhacker et al. | 29/451 |
| 5,437,288 | 8/1995 | Schwartz et al. | 128/772 |
| 5,573,520 | 11/1996 | Schwartz et al. | 604/282 |

*Primary Examiner*—Max Hindenburg
*Assistant Examiner*—Pamela L. Wingood
*Attorney, Agent, or Firm*—Fish & Richardson, P.C.

[57] ABSTRACT

The invention features a medical guidewire constructed for insertion into the body for providing access to a body passage. The medical guidewire has a main proximal portion in the form of an elongated tube extending the majority of the length of the guidewire, and a distal tubular portion integral with the main proximal portion. The distal portion includes a distal end and a flexible section having a slot cut in the wall of the distal tubular portion. The slot crosses the right sections of the distal tubular portion at an oblique angle and extends continuously about the distal tubular portion, in excess of at least one rotation about the distal tubular portion, to increase the flexibility of the distal tubular portion with respect to the main proximal portion.

26 Claims, 3 Drawing Sheets

ND GUIDEWIRE

BACKGROUND OF THE INVENTION

This invention relates to medical guidewires which are used by physicians to access body lumens or other remote areas within the body.

Guidewires are widely used in conjunction with therapeutic devices, such as catheters, which are threaded over the guidewire to gain access to an area within the body requiring diagnosis or treatment. Typically, a guidewire has a significantly smaller outer diameter than therapeutic devices and can therefore be inserted into the body to access remote areas more easily. When the guidewire is positioned at the desired location within the body, the therapeutic device is passed over and guided along the guidewire to the location. The therapeutic device is then utilized to diagnose and/or treat the area at the location.

SUMMARY OF THE INVENTION

This invention features a medical guidewire in the form of an elongated hollow tube, i.e., a tube with a continuous wall such as is formed by extrusion and drawing, having a sufficiently stiff proximal end, a flexible, atraumatic distal end, and a thin wall thickness to maximize the open area within the tubular structure of the medical guidewire. In one aspect, small lumens of the body can be accessed with a tubular guidewire according to the invention, by conventional guidewire techniques, and then an even smaller, subselective guidewire can pass through the open area of the initial guidewire to access even more restricted regions of the body. Furthermore, the relatively large open area within the medical guidewire, as compared to its small outer diameter, enables therapeutic means, such as liquid medicants, surgical instruments, or diagnostic tools, to pass through the medical guidewire to access a desired location within the body. Thus, small lumens of the body can be accessed through the tubular structure of the medical guidewire, using through the guidewire procedures, to provide certain types of diagnosis and/or treatment at the desired location within the body while also enabling access of conventional over-the-wire instruments. The small outer diameter of the medical guidewire of the invention enables conventional over-the-wire instruments to be used in conjunction with the guidewire.

In one aspect, the invention features a medical guidewire constructed for insertion into the body for providing access to a body passage, the guidewire having a main proximal portion in the form of an elongated tube extending the majority of the length of the guidewire, and a distal tubular portion integral with the main proximal portion. The distal portion includes a distal end and a flexible section having a slot cut in the wall of the distal tubular portion. The slot crosses the right sections of the distal tubular portion at an oblique angle and extends continuously about the distal tubular portion, in excess of at least one rotation about the distal tubular portion, to increase the flexibility of the distal tubular portion with respect to the main proximal portion.

In another aspect, the invention includes an elongated member having an outer diameter sized to pass through the medical guidewire such that the elongated member may be inserted through the main proximal portion and the distal tubular portion and extend beyond the distal end of the distal tubular section further into the body. In preferred embodiments, the elongated member is a subselective guidewire or an obturator.

In another particular aspect, the slot in the flexible section of the medical guidewire crosses the right sections of the distal tubular portion at an oblique angle and extends continuously through a plurality of rotations about the distal tubular portion to increase the flexibility of the distal tubular portion with respect to the main proximal portion.

Preferred embodiments include the following features.

The main proximal portion and the distal tubular portion are formed from nitinol and at least the distal tubular portion is annealed progressively to cause distal portions of the distal tubular portion to be more flexible than proximal portions thereof.

A subselective guidewire is used in combination with the medical guidewire and is sized to pass through the medical guidewire, through the main proximal portion and the distal tubular portion, to extend beyond the distal end of the distal tubular portion further into the body. The outer diameter of the main proximal portion is preferably of the order of 0.020 inches or smaller and the outer diameter of the subselective guidewire is preferably of the order of 0.014 inches or smaller.

The slot in the wall of the distal tubular portion extends continuously through a plurality of rotations about the tube, preferably through at least five rotations. The width of the slot may vary along the length of the slot such that the width is less in proximal portions of the slot, e.g., from about 0.001 inches to about 0.002 inches, relative to distal portions thereof, e.g., from about 0.004 inches to about 0.005 inches. Alternatively, the width of the slot may be constant, e.g., between about 0.002 inches to about 0.004 inches.

The oblique angle is greater at proximal portions of the slot than distal portions thereof and may decrease progressively, proximally to distally, along the slot, from about 45° to about 10°.

The distal tubular portion may further include a transition section, located proximally of the flexible section, that has portions of the wall of the distal tubular portion removed to impart an intermediate range of flexibility such that the transition section is more flexible than the main proximal portion and less flexible than the flexible section. The transition section includes at least one slot shorter than the slot in the flexible section. The transition section slot has a discontinuous slot section which includes a series of relatively short slots, generally helically aligned, separated by unslotted portions of the wall of the distal tubular portion. In aggregate, the discontinuous slot section extends more than one rotation about the distal tubular portion. The length of the discontinuous slot section and the length of the flexible section each extend about 2 to 3 cm of the length of the distal tubular body.

The transition section may further include a pattern of perforations through the wall of the distal tubular portion. The pattern of perforations is located proximally of the relatively short slot and extends about 3 to 5 cm of the length of the distal tubular portion. The pattern size and shape of the perforations are selected to cause the corresponding region of the distal tubular portion to be more flexible than proximal portions thereof and less flexible than distal portions thereof.

A sealing element extends along at least a portion of the distal tubular portion and is joined to the wall of the tubular member on both sides of the slot. The sealing element has at least one fluid-delivery perforation aligned with the slot to deliver fluids to a desired location within the body. The sealing element may be a polymeric tube, in shrunken state, that surrounds at least a portion of said distal tubular portion or may be a polymeric tube, in a radially expanded state, that contacts the inside of at least a portion of said distal tubular portion. Alternatively, an elastomer may fill at least a portion of the slot in said distal tubular portion.

A distal tip portion, located distally of the distal tubular portion, has a rounded distal extremity for atraumatic insertion into the body and is fabricated from a polymeric material chosen from the group comprising PET, polyimide, or polyethylene. The distal tip portion includes a polymeric core disposed within a polymeric sleeve which is attached to the polymeric core. The polymeric core and the polymeric sleeve are made from a nylon material and the polymeric core may further contain a radiopaque material. A nitinol core, having a tapered distal portion is disposed within the polymeric core and extends proximally through at least a portion of the distal tubular portion. The diameter of the nitinol core that extends into at least a portion of the distal tubular portion is smaller than the internal diameter of the distal tubular portion to provide a clearance between the nitinol core and the inner surface of said distal tubular portion.

Alternatively, the distal tip portion is hollow and includes a longitudinal slit in opposing walls of the distal tip portion. The longitudinal slit is biased closed and upon application of an internal force, i.e., a longitudinal thrusting force of an elongated member or fluid pressure, is capable of opening to provide a passageway through the distal tip portion.

Another aspect of the invention features a method of treating a patient using a medical guidewire that implements the structural features of the invention. The medical guidewire is inserted into a body lumen and the elongated member is inserted into the medical guidewire. The elongated member is sized to pass through the medical guidewire so that the elongated member may be inserted through the main proximal portion and the distal tubular portion of the medical guidewire. The medical guidewire and the elongated member are guided to a desired location in the body lumen requiring treatment and the elongated member is extended beyond the distal end of the medical guidewire, further into the body, to access remote, small passages at the desired location.

Preferred embodiments include the following features.

While the medical guidewire and the elongated member are guided to the desired location in the body lumen, the position of the elongated member within the medical guidewire is adjusted to alter the stiffness of the distal tubular portion of the medical guidewire.

Further, a surgical instrument may be slid, in guided contact, over the medical guidewire to access the desired location such that at least one surgical operation using the surgical instrument may be performed at the desired location.

In another aspect, the invention features a method of treating a patient using the medical guidewire of the invention. The medical guidewire is inserted into a body lumen and guided to a desired location in the lumen requiring treatment. Liquid is infused through the medical guidewire and exits the medical guidewire though the slot in the distal tubular portion of the medical guidewire to enter the body lumen at the desired location. The medical guidewire is removed from the body lumen.

Other features and advantages of the invention will become apparent from the following detailed description, and from the claims.

BRIEF DESCRIPTION OF THE DRAWINGS

FIG. 1 shows a medical guidewire according to the invention, while

FIG. 5 shows a side view of an embodiment of the medical guidewire, having a sealing element, while

FIGS. 8 and 8a are side views, partially in cross-sectional, of further embodiments of the medical guidewire of the invention, while

DESCRIPTION OF THE PREFERRED EMBODIMENTS

Figure 1:
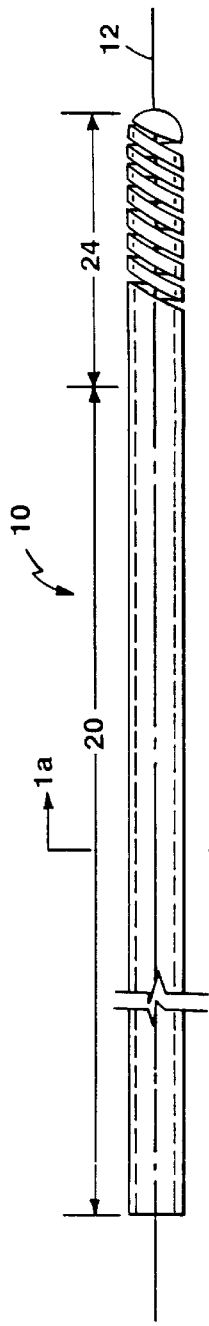
Figure 1A:
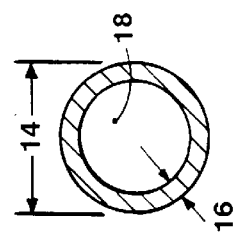
FIG. 1a is an enlarged cross-sectional view of the medical guidewire taken along line a—a in FIG. 1.

Referring to FIG. 1, a medical guidewire 10 is shown for use as a primary access device for entering a body lumen, particularly relatively small body lumens, such as, for example, the vasculature of the brain or distal coronary arteries. The overall length of the medical guidewire is about 180 to 220 cm.

The medical guidewire comprises a hollow tube defined by a continuous wall, such as can be formed by extrusion and drawing. The inner and outer diameters of the medical guidewire are sized to reduce the wall thickness of the guidewire to optimize the open area of the lumen within the guidewire. This construction facilitates the delivery of therapeutic means, such as, liquids, surgical instruments, or diagnostic tools, through the medical guidewire 10 while also providing the means for secondary access, i.e., by guiding a catheter over the medical guidewire to access the desired location. To maintain adequate strength, stiffness, and torque characteristics, the medical guidewire 10 is formed from a flexible and resilient metal, preferably nitinol.

In particular, the medical guidewire 10 has an outer diameter 14 of the order of 0.020 inches (0.51 mm) and a wall thickness 16 of the order of 0.002 inches (0.051 mm) to maximize the expanse of open area 18. Medical guidewire 10 is comprised of at least two integral portions, main proximal portion 20 and distal tubular portion 24. Main proximal portion 20 is about 165 cm to about 205 cm in length and is in the form of an elongated tube, i.e., an elongated hollow cylinder, and although flexible, has a stiffness of about 50–100 N-mm$^2$ to impart sufficient lateral stiffness and torque transmission capabilities along its length.

Figure 2:
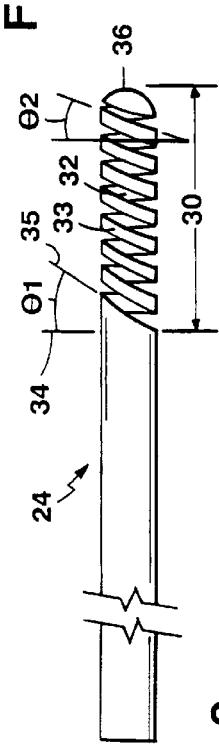
FIGS. 2–4 shows side views of embodiments of a portion of the medical guidewire of the invention.

Referring as well to FIG. 2, distal tubular portion 24 is located distally of main proximal portion 20 and is from about 15 to about 25 cm in length. Distal tubular section is also in the form of a tube and is integral with main proximal portion 20. For purposes of this invention, the term "integral" means that the distal tubular portion is attached to main proximal portion by a suitable method (e.g., by welding, brazing, heat shrinking, or gluing) in an end to end, abutting relationship or in an overlapping relationship. Alternatively, "integral" means that distal tubular portion and main proximal portion are fabricated from the same continuous tube, but comprise distinct portions in that tube. Distal tubular portion 24 has a stiffness of about 25–50 N-mm$^2$ or less, to impart flexibility to medical guidewire 10. Additionally, the flexibility of medical guidewire 10 may be varied by progressively annealing either a portion, e.g., distal tubular portion 24, or the entire length of medical guidewire 10.

Distal tubular portion 24 is comprised of flexible section 30 having slot 32. The length of flexible section 30 is about 2 to 3 cm. Slot 32 is preferably cut completely through wall 33 of distal tubular portion. Alternatively, to vary the stiffness of distal tubular portion 24, a portion of slot 32 may be replaced with a grooved section (not shown), which is only partially cut through the wall of distal tubular portion 24. In either embodiment, slot 32 crosses right sections, e.g., section 34, of the distal tubular portion at an oblique angle, e.g., angle Θ, and extends continuously for at least one rotation, preferably through a plurality of rotations, e.g., from about 3 to 15 rotations. It should be understood that right section 34 is perpendicular to the longitudinal axis 12 of medical guidewire 10 and that oblique angle Θ is an angle formed between right section 34 and the center axis of slot 32 (represented by line 35).

To vary the stiffness within flexible section 30, such that distal portions of flexible section 30 are more flexible than proximal portions thereof, oblique angle Θ is greater at proximal portions of slot 32 than distal portions thereof, e.g., oblique angle $Θ_1$ is greater than oblique angle $Θ_2$. The decrease of angle Θ proximally to distally is progressive, i.e., with each rotation about distal tubular portion 24, angle Θ decreases uniformly between 1 to 8° or more per rotation. Alternatively, angle Θ decreases variably, i.e., with each rotation, angle Θ decreases variably. Preferably, angle Θ varies from about 45° to about 10° proximally to distally.

Additionally, the stiffness of flexible section 30 may be varied by increasing the width of slot 32 proximally to distally. For example, the width of slot 32 at proximal portions of flexible section 30 is from about 0.001 inches to about 0.002 inches (0.0025 cm to about 0.051 mm) and the width of slot 32 at distal portions thereof is from about 0.004 inches to about 0.005 inches (0.102 mm to about 0.127 mm). Alternatively, the width of slot 32 may be constant, e.g., from 0.002 inches to 0.004 inches (0.051 mm to 0.102 mm).

Figure 3:
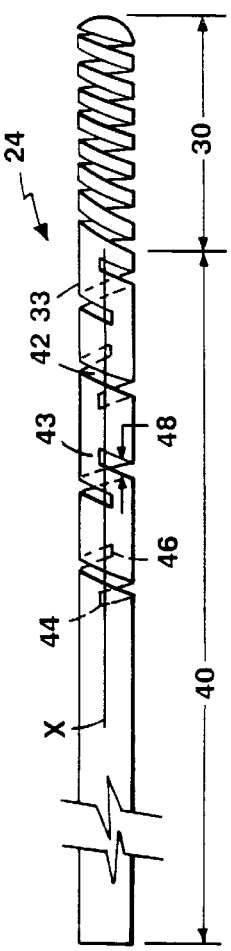

Referring now to FIG. 3, distal tubular section 24 may further comprise transition section 40, located proximally of flexible section 30. Portions of wall 33 in transition section 40 are removed to impart an intermediate range of flexibility to transition section 40, i.e., transition section 40 is more flexible than main proximal portion 20 and less flexible than flexible section 30. Wall 33 may be removed only partially, such as, for example, having a groove or a notch cut only partially through wall 33, or wholly, such as, for example, a slot cut completely through wall 33, or a combination of both. Transition section 40 includes at least one discontinuous slot 42, and preferably a plurality of discontinuous slots 42, separated by unslotted portions 43 of wall 33. Discontinuous slot 42 is preferably generally helically aligned about wall 33 of distal tubular portion 24 and proceeds through more than one rotation about distal tubular portion 24. In particular, if a reference line "X" is drawn on wall 33 parallel to longitudinal axis 12, discontinuous slot 42, having one end 44 beginning on or near reference line "X", proceeds generally helically about distal tubular portion 24 such that second end 46 is located past reference line "X", i.e., discontinuous slot 42 proceeds through more than one rotation about distal tubular portion 24.

The portion of transition section 40 having discontinuous slots 42 extends about 2 to 3 cm of the length of distal tubular section 24. Each discontinuous slot 42 has a length of about 0.03 inches to about 0.05 inches (0.076 cm to about 1.27 mm), preferably about 0.04 inches (1.02 mm). The distance between discontinuous slots 42, or the length of unslotted portion 42, is about 0.01 inches to about 0.1 inches (0.025 cm to about 0.25 cm). The pitch of discontinuous slot 42 is preferably about 45° and width 48 is preferably constant, between about 0.001 inches to about 0.002 inches (0.025 mm to about 0.051 mm). Alternatively, width 48 may vary as described above.

Figure 4:
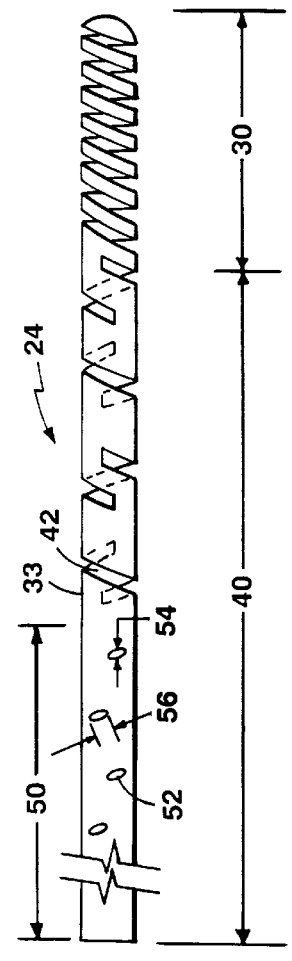

Referring to FIG. 4, transition section 40 may further comprise a pattern of perforations 50 through wall 33 of distal tubular section 24. The pattern of perforations is located proximally of discontinuous slots 42 and extends through a length of about 3 to 5 cm of the length of distal tubular section 24. The pattern size and shape of the perforations is selected such that the pattern of perforations 50 is less flexible than discontinuous slots 42 and more flexible than main proximal portion 20.

Pattern of perforations 50 consists of a plurality of angled slots 52, that are cut through wall 33. Alternatively, angled slots 52 may be only partially cut through wall 33 and may have various depths to alter the stiffness of distal tubular section 24 at pattern of perforations 50.

Angled slots 52 are oriented at a particular pitch, preferably 45°, and are disposed at 90° or 120° intervals along wall 33 of distal tubular portion 24. Width 54 of angled slots 52 is about 0.001 inches to about 0.005 inches (0.025 mm to about 0.127 mm). Length 56 of each angled slot 52 is about 0.020 inches (0.51 mm) and each slot is separated by a length of about 1.0 to about 1.5 mm. The desired degree of flexibility in the pattern of perforations 50 may be varied by varying slot width 54, slot length 56, and the distance between slots. Additionally, the shape of angled slots 52 may be varied to vary the flexibility.

Distal tubular portion 24 is preferably manufactured from a nitinol tube. To impart the desired flexibility characteristics to flexible section 30 and transition section 40, slots 32, 42, and 52 are formed into distal tubular portion 24 by, for example, EDM machining, chemical masking, electrochemical etching, or laser etching.

Figure 5:
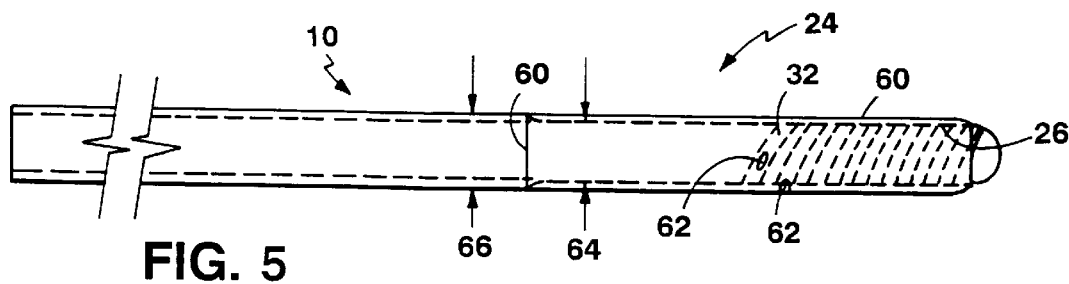

Referring to FIG. 5, a sealing element 60 seals and provides additional strength to medical guidewire 10. In the preferred embodiment, sealing element 60 is a sleeve that is heat shrunk to surround at least a portion of distal tubular portion 24. The thickness of sealing element 60 is about 0.0005 inches (0.013 mm) and is fabricated from either PET, polyimide, polyethylene, polyurethane, teflon, EVA, silicon, or hydrophilic gel. The outer diameter of distal tubular portion 24 is preferably reduced at portions including sealing element 60 such that the outer diameter of medical guidewire 10 remains constant. For example, distal tubular portion outer diameter 64 is less than distal tubular portion outer diameter 66 such that the outer diameter of medical guidewire 10 is not increased at portions including sealing element 60.

Figure 5A:
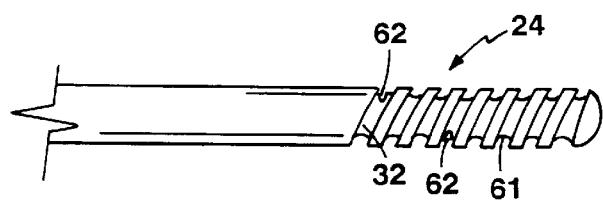
FIG. 5a shows a side view of an alternative embodiment of the sealing element.

Alternatively, sealing element 60 may be a sleeve that is radially expanded from inside medical guidewire 10 (not shown), to contact the inside wall 26 of at least a portion of distal tubular portion 24, or may be an elastomer 61 which fills at least a portion of the slots located in distal tubular portion 24 (FIG. 5a).

Sealing element 60 may include at least one fluid-delivery aperture 62, preferably a plurality of fluid-delivery apertures 62, aligned along slot 32. Additionally, if sealing element 60 covers a portion of slots 42 and/or 52 in transition section 40, fluid delivery perforations 62 are aligned along portions of these slots. Fluid-delivery apertures 62 enable a fluid to be infused through medical guidewire 10 and out through the fluid-delivery apertures 62 into a body lumen to the site of interest and are preferably about 1 to 5 mils in diameter. For example, the infused fluid may be a saline solution which can be used to flush the site of interest or to clean surgical instruments used in combination with the medical guidewire 10 during a surgical procedure or diagnosis. Alternatively, the fluid may be a liquid medicant to treat the site of interest or a radiographic or ultrasonic contrast agent to monitor fluid flow through the site of interest using, for example, x-ray or ultrasound techniques. Fluid-delivery apertures 62 are fabricated using a laser or a heated needle to perforate sealing element 60.

Figure 6:
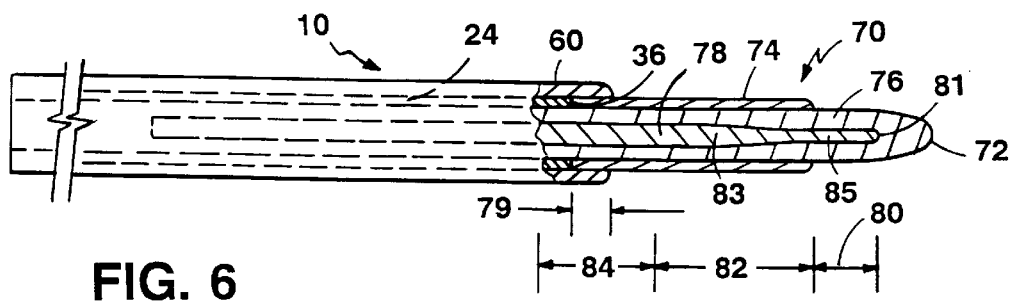
FIGS. 6 and 7 are side views, partially in cross-sectional, of embodiments of the medical guidewire of the invention.

Referring to FIG. 6, in one embodiment, a distal tip portion 70 is attached to distal tubular portion 24. To enable atraumatic insertion of medical guidewire 10 into the body, distal tip portion 70 is flexible, is about 5 inches to about 3 inches (1.27 cm to about 7.62 cm) long, and has a rounded distal extremity 72, the outer diameter of which is about 0.014 inches (0.356 mm). Distal tip portion 70 includes sleeve 74 which abuts distal end 36 of distal tip portion 24. The inner and outer diameter of distal tubular portion 24 at distal end 36 is substantially similar to the inner and outer diameter of sleeve 74. Sleeve 74 further surrounds core 76. Core 76 encases tapered core 78. Sleeve 74 and core 76 are made from a polymeric material, preferably nylon. Further, the availability of a range of stiffness for sleeve 74 and core 76 permits the overall stiffness of distal tip portion 70 to be tailored to the desired end use of medical guidewire 10. Additionally, core 76 may be filled with a radiopaque material so that a physician can view its position within the body using an x-ray.

To attach distal tip portion 70 to distal tubular portion 24, sealing element 60 surrounds a portion 79 of the proximal end of sleeve 74. Sleeve 74 is bonded to core 76, and core 76 is bonded to tapered core 78, preferably with flexible adhesives, such as, for example, urethane.

Tapered core 78 is approximately 6–10 cm in length and preferably has three sections, distal section 80, tapered section 82 and proximal section 84. Distal section 80 is approximately 1 to 2 cm in length, preferably 1 cm, and has a constant diameter, which is preferably about 3 to 4 mils (about 0.076 mm to 0.101 mm). Tapered section 82 is located proximally of distal section 80 and is also preferably about 1 to 2 cm in length. The proximal end 83 of tapered section 82 has the largest diameter of tapered core 78, e.g., about 6 mils (0.152 mm), and tapers uniformly to distal end 85 of tapered section 82, where the diameter is about 3 mils (0.076 mm). Alternatively, tapered core 78 may have a constant diameter. Proximal section 84 is located proximally of tapered section 82 and is about 4 to 6 cm in length and extends proximally through a portion of distal tubular portion 24. The diameter of proximal section 84 is substantially the same as the diameter of the proximal end 83 of tapered section 84, i.e., about 6 mils (0.152 mm). Therefore, there is clearance between the inner diameter of distal tubular portion 24 and the proximal section of tapered core 78 to enable the passage of fluids. Preferably, tapered core 78 is fabricated from a solid nitinol wire.

Figure 7:
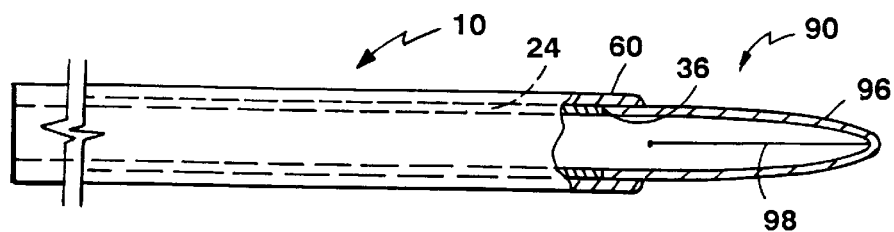

Referring to FIG. 7, in an alternative embodiment, distal tip portion 90 comprises duck bill 96 bonded to sealing element 60 by, for example, a flexible adhesive, such as urethane. Duck bill 96 is fabricated from a polymeric material (e.g., PET, polyimide, or polyethylene) and includes a longitudinal slit 98 in opposite walls of distal tip portion 90. Longitudinal slit 98 is biased closed, however, upon an application of an internal force, such as, for example, fluid pressure or a longitudinal thrusting force, longitudinal slit 98 opens to provide a passageway through distal tip portion 90.

Figure 8:
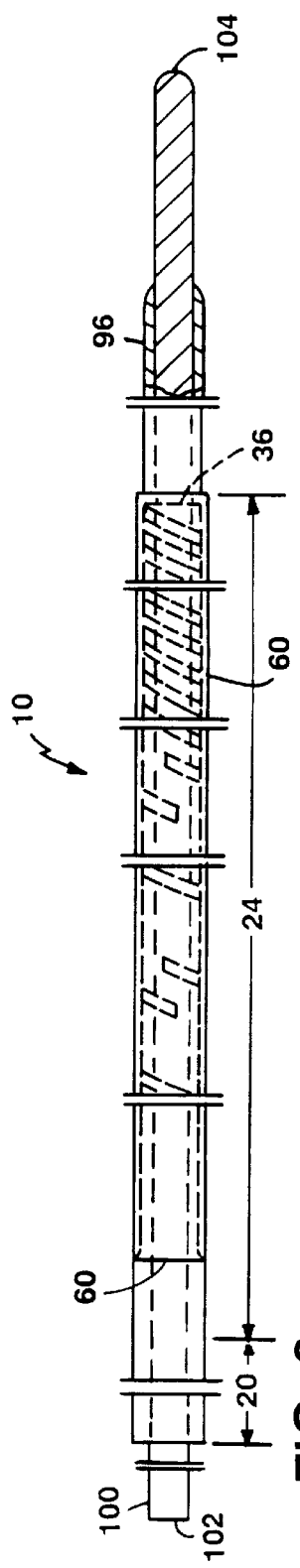

Referring to FIG. 8 et seq., medical guidewire 10 includes elongated member 100, which is inserted through main proximal portion 20 and distal tubular portion 24 and may, in certain applications, be extended beyond distal end 36 of distal tubular portion 24 further into the body. To enable the insertion of elongated member 100 through medical guidewire 10, for coronary, neurology, or urology applications, elongated member 100 has an outer diameter of the order of 0.014 inches (0.356 mm) or smaller and the outer diameter of the medical guidewire is of the order of 0.020 inches (0.051 cm) or smaller. Alternatively, for cardiac, gastro-intestinal, or peripheral vascular applications, elongated member has an outer diameter of the order of 0.03 inches (0.076 cm) or smaller and the outer diameter of medical guidewire is of the order of 0.035 inches (0.089 cm) or smaller. The length of elongated member 100 is typically about 180 to 220 cm, or more. This length is sufficiently long to enable a user to manipulate elongated member 100 at proximal end 102 and still provide sufficient length at distal portion 104 such that elongated member can extend beyond distal end 36 of distal tubular portion 24 further into the body.

Figure 8A:
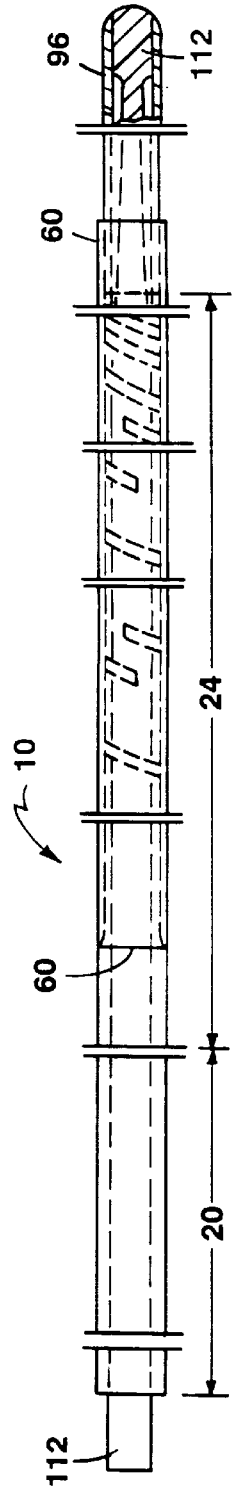
Figure 8B:
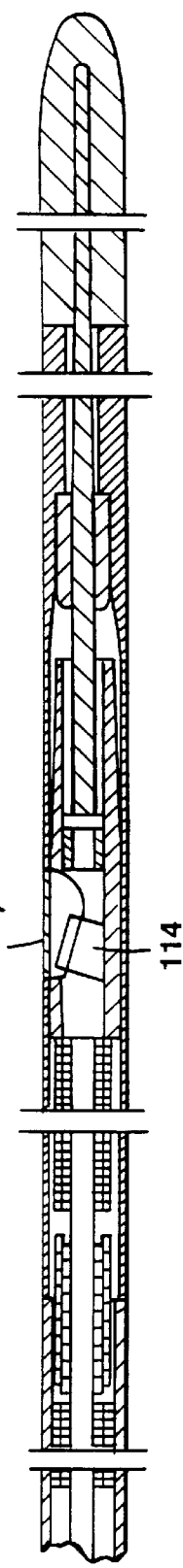
FIG. 8b shows a cross-sectional view of a further embodiment of the medical guidewire of the invention.

In a preferred embodiment, elongated member 100 is a subselective guidewire, as shown in FIG. 8, preferably formed from a solid nitinol wire, but alternatively, formed from a nitinol coil. Alternatively, elongated member 100 is an obturator 112 (FIG. 8a) or an ultrasound imaging transducer 114 (FIG. 8b—To enable the passage of ultrasonic sound waves through medical guidewire 10, a sonolucent window 115 may be located in distal tubular portion 24 or distal tip portion 70 may be fabricated from a sonolucent material). Additionally, elongated member 100 may be in the form of other surgical or diagnostic instruments, such as, for example, a basket retrieval system, a surgical instrument (e.g., a cutter), a laser fiber, an optical fiber, a balloon, a radioactive element, an antenna, or an electrode or series of electrodes.

Method of Use

A user inserts medical guidewire 10 into a body lumen using, for example, the Seldinger technique. Preferably, to increase the stiffness of medical guidewire 10, elongated member 100 is inserted through medical guidewire 10 prior to inserting medical guidewire 10 into the body lumen. The medical guidewire, including elongated member 100, is guided within a body lumen to a location within the body lumen requiring treatment. As medical guidewire 10 is guided within a body lumen, a user manipulates elongated member 100 along longitudinal axis 12 within distal tubular portion 24 to vary the stiffness of medical guidewire 10 at distal tubular portion 24. When medical guidewire 10 is positioned at or near the location within the body lumen requiring treatment, the user, by manipulating the proximal end of elongated member 100, extends elongated member 100 beyond distal end 36 of distal tubular section 24 further into the body. The elongated member 100 thus accesses remote, small passages at the desired location for diagnosis and/or treatment of the area. For example, in the illustrated embodiment, elongated member 100 is a subselective guidewire, which enables a user to access more distal or tortuous regions of the body. Other surgical instruments or diagnostic or therapeutic means used within small lumens of the body may be employed as elongated member 100 to perform their respective procedures at the desired location.

Alternatively, after medical guidewire 10 is guided to a desired location within the body, medical guidewire 10 is used to infuse liquids to that location. For example, liquids, such as saline solution, medicants, or x-ray contrast liquids, are infused through slot 32, through slots 32, 42 and 52, through fluid-delivery apertures 62 (when distal tubular portion includes sealing element 60), through open distal end 36, and/or through longitudinal slit 98 in distal tip portion 90.

Medical guidewire 10 may further be used to guide surgical or diagnostic instruments over medical guidewire 10 to access a desired location in a body lumen. When the instrument is positioned at the desired location within the body lumen, at least one surgical or diagnostic procedure using the instrument is performed. The instrument may be removed and replaced with a different instrument as required by the treatment, diagnosis, or surgical procedure being performed by the user.

What is claimed is:

1. A medical guidewire constructed for insertion into the body for providing access to a body passage, comprising:
   a main proximal portion in the form of an elongated tube, said tube extending the majority of the length of the guidewire, and
   a distal tubular portion integral with said main proximal portion and having a distal end, said distal portion including a flexible section having at least one slot cut in the wall of said distal tubular portion, said slot crossing the right sections of said distal tubular portion at an oblique angle, said slot extending continuously about said distal tubular portion through a plurality of rotations about said distal tubular portion, said oblique angle being greater at proximal portions of said slot than distal portions thereof.

2. The medical guidewire of claim 1, in combination with an elongated member sized to pass through said medical guidewire, whereby said elongated member may be inserted through said main proximal portion and said distal tubular portion of the medical guidewire and extend beyond said distal end of said distal tubular portion further into the body.

3. The medical guidewire of claim 2, wherein said elongated member is a guidewire.

4. The medical guidewire of claim 2, wherein said main proximal portion has an outer diameter of the order of 0.020 inches or smaller and said elongated member has an outer diameter of the order of 0.014 inches or smaller.

5. The medical guidewire of claim 1, wherein said slot extends continuously through at least five rotations.

6. The medical guidewire of claim 1, wherein said oblique angle decreases progressively, proximally to distally, along said slot.

7. The medical guidewire of claim 6, wherein said oblique angle varies from about 45° to about 10° proximally to distally along said slot.

8. The medical guidewire of claim 1, wherein said main proximal portion and said distal tubular portion are formed from nitinol.

9. The medical guidewire of claim 1, wherein the width of said slot varies along the length of said slot whereby the width of said slot is less in proximal portions of said slot relative to distal portions thereof.

10. The medical guidewire of claim 9, wherein the width of said slot varies from about 0.001 inches to 0.002 inches to about 0.004 inches to 0.005 inches.

11. The medical guidewire of claim 1, wherein the width of said slot is constant and is between about 0.002 inches to about 0.004 inches.

12. The medical guidewire of claim 1, wherein said distal tubular portion includes a transition section located proximally of said flexible section, said transition section having portions of said wall removed to impart an intermediate range of flexibility such that said transition section is more flexible than said main proximal portion and less flexible than said flexible section.

13. The medical guidewire of claim 12, wherein said transition section includes at least one slot shorter than said slot of said flexible section.

14. The medical guidewire of claim 13, wherein said slot of said transition section comprises a discontinuous slot section having a series of relatively short slots generally helically aligned, separated by unslotted portions of the wall of said distal tubular portion and, in aggregate more than one rotation about said distal tubular portion.

15. The medical guidewire of claim 13, wherein said transition section further includes a pattern of perforations through said wall of said distal tubular portion, said pattern of perforations is located proximally of said relatively short slot and extends about 3 to 5 cm of the length of said distal tubular portion, the pattern size and shape of said perforations being selected to cause the corresponding region of said distal tubular portion to be more flexible than proximal portions thereof and less flexible than distal portions thereof.

16. The medical guidewire of claim 1, wherein at least said distal tubular portion is annealed progressively to cause distal portions of said distal tubular portion to be more flexible than proximal portions thereof.

17. The medical guidewire of claim 1, further comprising a sealing element extending along at least a portion of said distal tubular portion, said sealing element being joined to the wall of said tubular member on both sides of said slot.

18. The medical guidewire of claim 17, wherein said sealing element has at least one fluid-delivery perforation aligned with said slot.

19. The medical guidewire of claim 1, further comprising a distal tip portion distal of said distal tubular portion, said distal tip portion having a rounded distal extremity for atraumatic insertion into the body.

20. The medical guidewire of claim 19, wherein said distal tip portion is hollow and includes a longitudinal slit in opposing walls of said distal tip portion, said longitudinal slit being biased closed and upon application of an internal force, capable of opening to provide a passageway through said distal tip portion.

21. A system for insertion into the body for providing access to a body passage, said system comprising:
   a main proximal portion in the form of a continuous hollow tube, said tube extending the majority of the length of the guidewire,
   a distal tubular hollow portion integral with said main proximal portion and having a distal end, said distal portion including a flexible section having a slot cut in the tubular wall of said distal tubular portion, said slot crossing the right sections of said distal tubular portion at an oblique angle, said slot extending continuously about said distal tubular portion through a plurality of rotations about said distal tubular portion, said oblique angle being treater at proximal portions of said slot than distal portions thereof, and
   an elongated member, said elongated member having an outer diameter sized to pass through said medical guidewire, whereby said elongated member may be inserted through said main proximal portion and said distal tubular portion of the medical guidewire and extend beyond said distal end of said distal tubular section further into the body.

22. The medical guidewire of claim 21, wherein said elongated member is a guidewire.

23. A method of treating a patient, comprising:
   providing the medical guidewire of claim 1 wherein said distal end is open;
   inserting said medical guidewire into a body lumen;

inserting an elongated member into said medical guidewire, said elongated member being sized to pass through said medical guidewire, whereby said elongated member may be inserted through said main proximal portion and said distal tubular portion of the medical guidewire;

guiding said medical guidewire and said elongated member to a desired location in said body lumen requiring treatment;

extending said elongated member beyond said distal end of said medical guidewire further into the body; and accessing remote, small passages at said location with said elongated member.

24. The method of claim 23, further comprising:

while guiding said medical guidewire and said elongated member to a location in said body lumen, adjusting the position of said elongated member within said medical guidewire to alter the stiffness of said distal tubular portion of said medical guidewire.

25. The method of claim 23, further comprising:

sliding a surgical instrument in guided contact over said medical guidewire;

accessing said location with said surgical instrument; and performing at least one surgical operation using said surgical instrument at said location.

26. A system for insertion into the body for providing access to a body passage, said system comprising:

a main proximal portion in the form of a continuous hollow tube, said tube extending the majority of the length of the guidewire, a distal tubular hollow portion integral with said main proximal portion and having a distal end, said distal portion including a flexible section having a slot cut in the tubular wall of said distal tubular portion, said slot crossing the right sections of said distal tubular portion at an oblique angle, said slot extending continuously about said distal tubular portion, in excess of at least one rotation about said tubular portion, to increase the flexibility of said distal tubular portion with respect to said main proximal portion, a distal tip portion distal of said distal tubular portion, said distal tip portion being hollow and including a longitudinal slit in opposing walls of said distal tip portion, said longitudinal slit being biased closed and upon application of an internal force, capable of opening to provide a passageway through said distal tip portion.

* * * * *